US008142379B2

(12) United States Patent
Verdonk et al.

(10) Patent No.: US 8,142,379 B2
(45) Date of Patent: *Mar. 27, 2012

(54) ORTHOPEDIC ARM AND SHOULDER BRACE

(75) Inventors: René Verdonk, Ghent (BE); Lieven De Wilde, Ghent (BE); Johan Berte, Kersbeek-Miskom (BE)

(73) Assignee: Universiteit Gent (BE)

( * ) Notice: Subject to any disclaimer, the term of this patent is extended or adjusted under 35 U.S.C. 154(b) by 537 days.

This patent is subject to a terminal disclaimer.

(21) Appl. No.: 11/937,289

(22) Filed: Nov. 8, 2007

(65) Prior Publication Data

US 2009/0048549 A1 Feb. 19, 2009

Related U.S. Application Data

(63) Continuation of application No. 10/661,238, filed on Sep. 12, 2003, now Pat. No. 7,354,412.

(30) Foreign Application Priority Data

Sep. 12, 2002 (EP) .................................... 02447173

(51) Int. Cl.
*A61F 5/00* (2006.01)

(52) U.S. Cl. .................. 602/16; 602/20; 602/13; 601/5; 601/33

(58) Field of Classification Search .................... 602/16, 602/32, 33, 20, 13; 601/5, 33, 23–24, 26, 601/16, 27, 29, 31, 34–35, 89, 92–93; 128/845, DIG. 20, 878; 482/44, 124
See application file for complete search history.

(56) References Cited

U.S. PATENT DOCUMENTS

| | | | | |
|---|---|---|---|---|
| 2,777,439 | A * | 1/1957 | Tuttle | 601/27 |
| 4,577,623 | A * | 3/1986 | Pecheux | 601/34 |
| 4,651,719 | A * | 3/1987 | Funk et al. | 601/33 |
| 4,665,899 | A * | 5/1987 | Farris et al. | 601/33 |
| 4,930,497 | A * | 6/1990 | Saringer | 601/34 |
| 5,236,411 | A * | 8/1993 | Backman | 602/13 |
| 5,665,058 | A * | 9/1997 | Young | 602/20 |
| 5,738,636 | A * | 4/1998 | Saringer et al. | 601/5 |
| 7,101,347 | B2 * | 9/2006 | Culhane et al. | 602/5 |

* cited by examiner

*Primary Examiner* — Patricia Bianco
*Assistant Examiner* — Camtu Nguyen
(74) *Attorney, Agent, or Firm* — Barnes & Thornburg LLP

(57) ABSTRACT

The present invention relates to a portable device for providing continuous passive motion of a limb comprising a brace for supporting said limb. A programmable motor, mechanically connected to the brace, provides continuous passive motion of a limb. The movement of the limb is controlled in two control points of movement at the lower arm. Flexible positioning means are provided with a fastening means positioning the brace and the programmable motor on the body of a person carrying said device in a stable position. The programmable motor is partially housed within the positioning means. The invention is particularly suitable for use in paramedical and orthopedic applications. It allows adduction and abduction, rotation and exo/endo rotation of a limb.

5 Claims, 5 Drawing Sheets

ORTHOPEDIC ARM AND SHOULDER BRACE

RELATED APPLICATION

This application is a continuation of U.S. patent application Ser. No. 10/661,238, filed Sep. 12, 2003, now U.S. Pat. No. 7,354,412.

FIELD OF THE INVENTION

The present invention relates to an orthopedic portable arm and shoulder brace providing continuous passive motion of a user's shoulder as well as methods of operating and designing such an orthopedic arm and brace.

BACKGROUND OF THE INVENTION

The shoulder is a relatively complex body joint having several degrees of freedom and ranges of linear and especially angular motion, i.e., abduction, flexion and rotation. Treatment of a shoulder following an injury or surgical trauma typically requires immobilization of the shoulder, and the arm connected to it, for an extended period of time.

Splint-type devices have been reported for immobilizing and supporting an injured shoulder during the healing process. U.S. Pat. No. 4,896,660 describes an arm support device comprising an upper arm support, a contoured well shoulder anchor, and a lower arm support. The upper arm support is operable to abut against a patient's side and underlies the humeral portion of a patient's arm. The contoured well shoulder anchor includes a contoured sleeve portion and two straps, which releasably connect the well shoulder anchor to the upper arm support. The lower arm support connects to the upper arm support structure and provides support for a patient's forearm and hand. FR 2,727,007 describes an inflatable cushion structure provided with different positioning means, which is applied between a patient's chest and his/her upper arm. FR 2,589722 and U.S. Pat. No. 5,423,333 describe a device for immobilizing a human shoulder, and for supporting the wrist of the arm associated with that shoulder, comprising three inflatable bladders joined together to form a triangular wedge. The wedge is positioned underneath the patient's arm such that one bladder is positioned along the patient's side, and such that the patient's arm rests on another of the bladders. The device is designed in such a way that the patients' arm is maintained in a fixed angle in relation to the thorax of the patient. The angle between the arm and the thorax support is variable, depending on the possibility to fold one of the bladders of the triangular wedge. U.S. Pat. No. 5,236,411 relates to a device for immobilizing the limb of a patient in an elevated position comprising an inflatable member that is adjustable between a deflated state and an inflated state and a harness for attaching the device to the body of a patient. The member is placed between a support surface and the limb of the patient, thus elevating the limb.

Nevertheless, although the above-described devices are suitable for immobilizing a shoulder, they immobilize the shoulder in essentially one position against the body: the arm is immobilized in a particular angle in relation to the thorax, and no further movement of the arm is allowed. Also, these devices do not enable the embraced arm and shoulder to undergo combined movements, which are useful for effective reinforcement of arm and shoulder muscles after injury or surgical operations.

In fact, it has been found that effective rehabilitation requires the recovery of the ranges of angular arm and shoulder motion. A certain degree of mobility of the patient's limbs is required in order not to detract from rehabilitation of the shoulder. In view of this requirement, devices have been developed which enable continuous passive motion of the patient's arm and shoulder of which EP 597,623 and EP 525,930 may be cited as examples.

EP 597,623 relates to an adjustable shoulder brace mountable on the arm and torso to isolate the shoulder and which is fully adjustable across the abduction, flexion and rotation ranges of motion of the shoulder so that it enables fixation of the shoulder in virtually any rehabilitative position. The brace is made up of a series of rigid support members secured to the body of the patient, and a plurality of selectively rotatable and lockable joints adjustably interconnecting the support members. It is said that the combined effect of the joints simulates the entire range of motion of the shoulder. However, due to the presence of a plurality of joints for positioning the shoulder at selected angles of abduction, flexion and rotation, the device is very complex, uncomfortable and difficult to adjust. Also, this device immobilizes the patients' shoulder at a selected angle.

EP 525,930 relates to a passive shoulder exerciser constructed to move a patient's arm back and forth through an arc of up to 180 degrees for providing flexion and abduction of the shoulder. The shoulder exerciser includes a base, an electric drive motor, and an arm holder for the patient's arm, mounted to the drive motor for reciprocal movement by the drive motor through an arc of up to 180 degrees. The arm holder is slidably and pivotably mounted such that during use of the exerciser a patient's arm may slide towards and away from the body and pivot along two pivot points to allow the shoulder joint to follow a natural anatomical range of motion. However, this type of device does not allow all of the essential movements, including combined movements of wrist and elbow. Furthermore, this device is cumbersome and unpractical. As it is not a portable device, the patient needs to go to the location of this exercise and rehabilitation device every time he wishes to use it.

Another shoulder device meant to impart continuous passive motion to a patient's shoulder is described in U.S. Pat. No. 4,651,719. A portable arm and shoulder brace causes abduction and adduction and has the option of causing simultaneous rotation as well through use of a single actuator. An upper arm support is pivotally connected to and extends laterally from the base of the device. A linear actuator extends between and is linked to the upper arm support and the base to cause abduction and adduction of the arm. A forearm support, which is pivotally connected to the upper arm support and angularly adjustable relative to the upper arm support, is linked to the base to cause rotation of the forearm support as the upper arm support is pivoted. The device is contained in a housing having a chamber with an extendable, two-part cover so that the operating mechanism is concealed. However, although portable, this device is rather large and can be uncomfortable.

Many of the above systems also have the disadvantage that they slide off of the body, sliding to the backside of the user which makes them not practical in use.

The presently known devices have several drawbacks. There remains a need for a compact and comfortable orthopedic brace that enables all kind of single as well as combined passive movements of the embraced limb.

SUMMARY OF THE INVENTION

It is an object of the invention to provide a brace providing continuous passive motion and overcoming the drawbacks of the presently known devices as well as a method of operating and designing such a brace.

It is also an object of the invention to provide an autonomous device suitable for embracing a limb, which is able to perform a number of different passive limb movements in an automated and controlled way.

It is also an object of the present invention to provide a device suitable for embracing a limb, which enables single as well as combined movements of the limb.

Another object of the invention consists of providing a limb brace, which is compact, easy to use and comfortable when mounted on a patient, even for extended periods of time.

It is another object of the present invention to provide a brace that increases the patient's ability to move around.

It is yet still a further object of the invention to provide a brace, which will effect any combination of the foregoing objects.

The invention is particularly suitable in the field of paramedical and orthopedic applications. In particular the invention can be used for the rehabilitation of all kind of injuries, especially of shoulder injuries.

The invention relates to a portable device suitable for providing continuous passive motion of a limb comprising a brace for supporting the distal end of the limb, a drive mechanism for providing a settable continuous passive motion of the limb, the drive mechanism being (mechanically) coupled to the brace and controlling movement of the distal end of the limb characterized in that the passive motion is controlled by a first control point of movement and a second control point of movement on the distal end of the limb and the drive mechanism comprises at least a first unit for controlling movement of the first control point of movement of the distal end of the limb. The portable device furthermore can comprise a second unit for controlling the movement of the second control point (of movement) of the distal end of the limb. In another embodiment the portable device comprises means for immobilizing the second control point (of movement) of the distal end of the limb.

The portable device furthermore can have flexible positioning means provided with a fastening means positioning the brace and the drive mechanism on the body of a patient carrying the device in a stable position, whereby the drive mechanism is at least partially housed within the positioning means.

The drive mechanism for providing a settable continuous passive motion of the limb can be a programmable motor.

In a further embodiment, the brace comprises a support for the distal end of the limb comprising a first primary sub-frame for supporting the distal end of the limb, a support for the proximal end of the limb comprising a second primary sub-frame for supporting the proximal end of the limb, and a hinge for connecting the support for the distal end of the limb to the support for the proximal end of the limb.

The portable device can have a brace comprising a secondary sub-frame connected to the first primary sub-frame of the distal end of the limb by means of a mechanical interface, the secondary sub-frame linking the first control point of movement with the second control point of movement. Furthermore, the mechanical interface is provided near a joint between the distal end and the proximal end of the limb and connecting the secondary sub-frame to the primary sub-frame of the distal end of the limb.

The portable device can furthermore comprise positioning means having an inflatable housing of flexible material provided with a fastening means, the housing allowing at least partial deformation when fastened on a body for providing a stable position. The supports for the distal end of the limb and the proximal end of the limb can be provided with limb fasteners, which may have fixing straps. The lower arm support may furthermore be adjustable in order to fit the length of the distal end of the limb of the user.

The first and second motor unit may consist of a triple spindle with electromotor with worm wheel transfer, being provided in a housing, allowing the motor units to induce a substantially vertical movement.

The mechanical interface may be provided with a motor-driven sliding mechanism, the mechanism allowing the support of the distal end of the limb to perform a sliding movement. The positioning means may further comprise belts provided with fasteners, for positioning said device on a body. The passive movements provided by the device may be controlled with a remote control unit, which may have control switches and a visual display screen. There may be provided two connectors at the upper side of the positioning means, whereby one connector is connected to the remote control unit and the other connector is connected to an electric transformer or one or more batteries.

The portable device can provide passive limb movements in an automated way.

In an alternative embodiment, the control points are connected to the positioning means e.g. by springs. In this way, active movements of the limb are limited due to the presence of the springs. This can be advantageous for e.g. training a limb, avoiding injuries due to excessive movement.

The invention relates to a portable device suitable for providing continuous passive motion of a limb, whereby the device comprises a brace for supporting a distal end of the limb, a drive mechanism for providing settable continuous passive motion of the limb, the drive mechanism being mechanically coupled to the brace in at least a first and a second control point for controlling movement of the distal end of the limb characterized in that the drive mechanism comprises means for providing at least adduction and abduction movements of the limb and rotational movements around at least the first or the second control point.

The present invention provides a device able to provide different motor-driven passive movements of a limb. The presence of a programmable motor mechanism in the device allows an embraced limb to undergo passive movements in an automated and controlled way. The programmable motor mechanism comprises several units, which induce vertical or sliding movements. Due to its ability to induce several types of movements, the device according to the invention is particularly suitable for providing single, as well as combined movements of the limb. Surprisingly, although the limb of a patient is effectively supported and immobilised in the device according to the invention, the limb still can undergo single as well as combined passive movements, said movements being recommended for effective rehabilitation of the injured limb.

Importantly, the device according to the invention is highly comfortable, as the device is portable, light and easy to apply. Moreover, the device is highly adaptable according to the anatomy of a patient carrying the device and is provided with a comfortable, flexible positioning means for applying the device on a patients' body. Also, because the motor unit of the device is at least partially provided in the positioning means, the device remains compact and comfortable from a patients' point of view. Surprisingly, bringing the motor mechanism of the device in the positioning means does not hinder the functionality neither from the motor mechanism, nor from the positioning means. Providing the motor mechanism of the device in the positioning means, at least partially, still enables the device to induce a series of different motor-driven passive limb movements. Also, although the positioning means is provided with at least a part of the motor mechanism, it still effectively positions the device on the body of a person carrying said device. In addition, as the device according to the invention is portable; the movement facilities of a patient carrying the device are not restricted.

Other objects and advantages of the present invention will become apparent from the following detailed description taken in conjunction with the accompanying drawings.

DETAILED DESCRIPTION OF THE FIGURES

Figure 6:
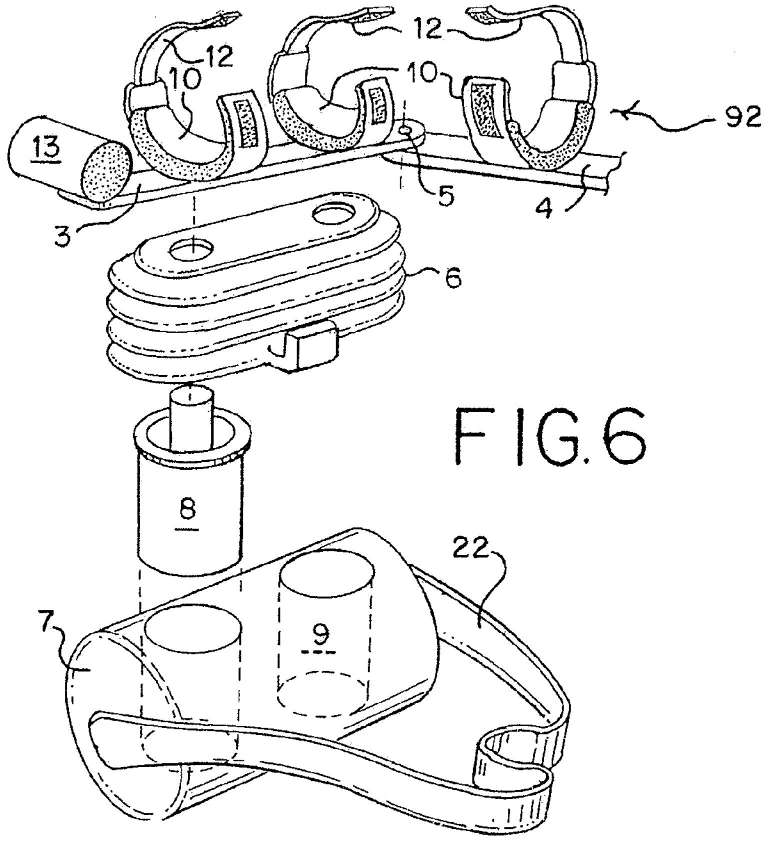

FIG. 6 provides a three-dimensional representation of a portable device according to a further embodiment of the invention, comprising a lower arm support, an upper arm support, a motor mechanism and positioning means with a fastening belt.

Figure 7:
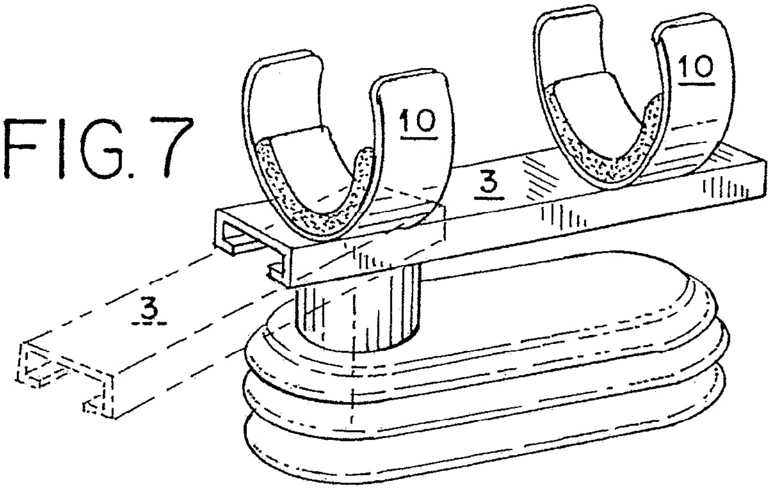

FIG. 7 represents a detailed view on a lower arm support according to an embodiment of the invention with arm fasteners.

Figure 8:
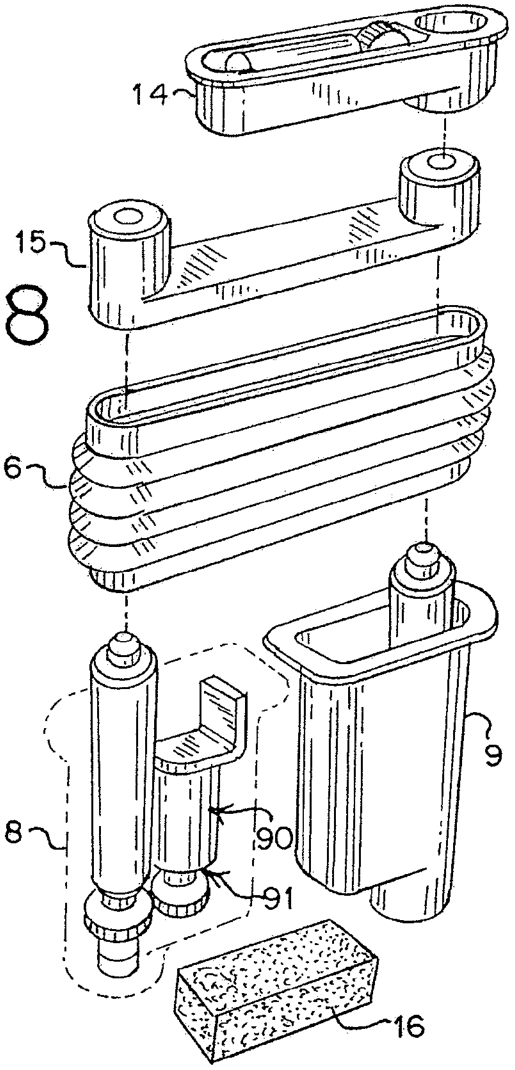

FIG. 8 is an exploded view of the motor mechanism of a device according to an embodiment of the present invention, comprising a hinge-like mechanical interface comprising a sliding motor unit provided in a housing. The mechanical interface is connected with a secondary sub-frame and with the motor units, that are at least partially incorporated in a bellows structure. This hinge-like mechanical interface is linked to one of the motor units.

Figure 9:
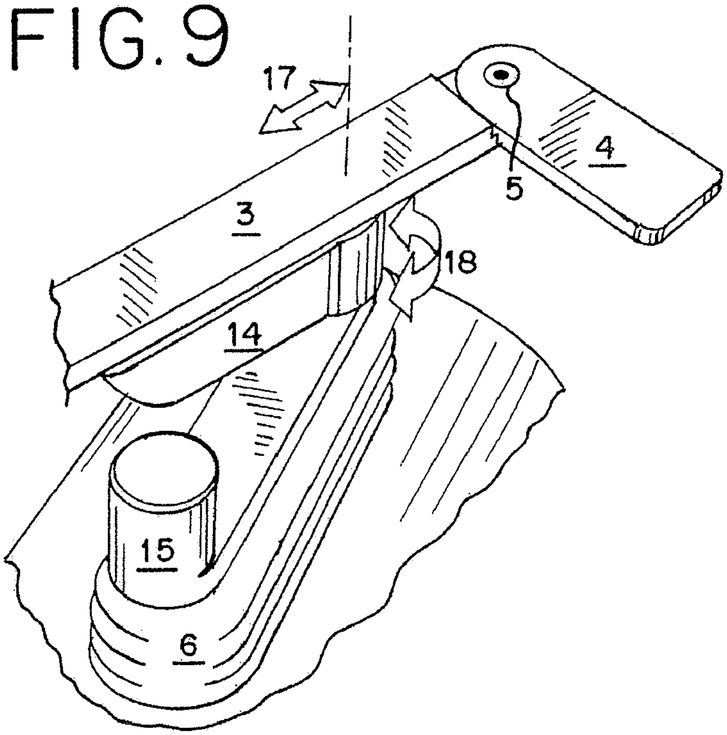

FIG. 9 illustrates the motor-driven translation movement, according to an embodiment of the invention, as indicated with arrow 17; and the not motor-driven endo/exo rotational movements, as represented with arrow 18.

Figure 10:
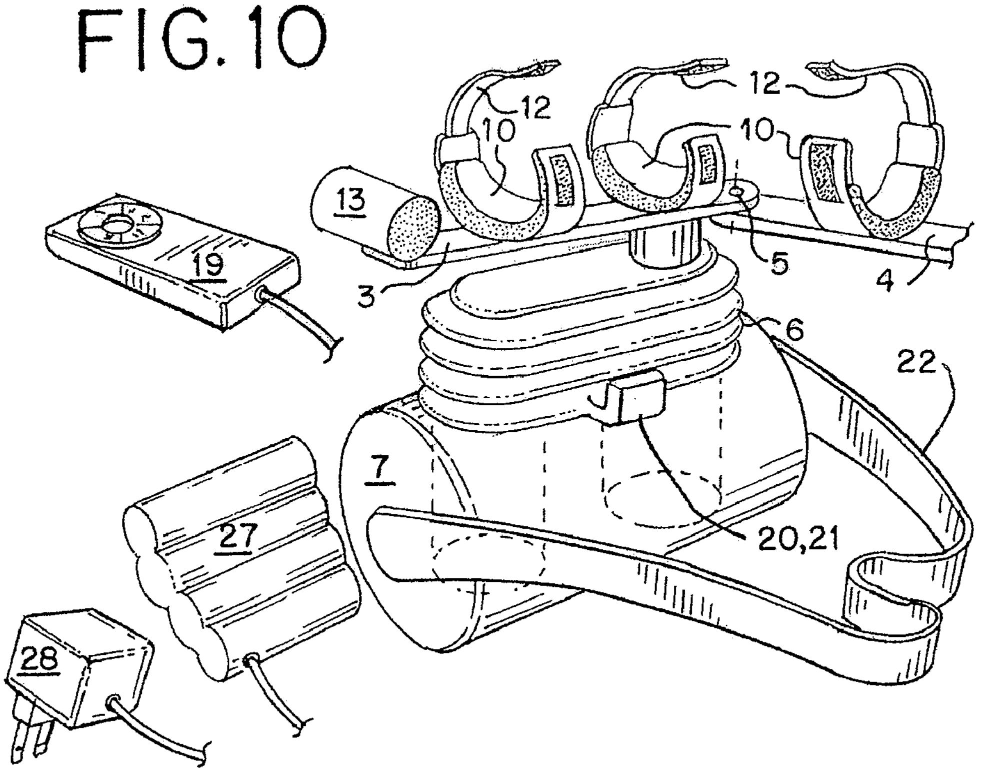

FIG. 10 depicts a device according to an embodiment of the invention provided with a remote control unit and two connectors at the upper side of the air chamber, one for a transformer or batteries and another for a remote control.

DETAILED DESCRIPTION OF THE INVENTION

The present invention will be described with respect to particular embodiments and with reference to certain drawings but the invention is not limited thereto but only by the claims. The drawings described are only schematic and are non-limiting. In the drawings, the size of some of the elements may be exaggerated or distorted and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

It is often necessary for orthopedic specialists to secure one or more limbs of a human or animal patient against movement following injury or treatment of the limb or limbs. Moreover, procedures involving surgery of a limb often necessitate post-surgical immobilization, which facilitates recovery and helps to prevent further injury during the recovery period. However, in addition, the injured limb also needs to undergo some movements, in order to reinforce its muscles and in order to facilitate its rehabilitation. The present invention provides a device that complies with both requirements.

The device of the invention is applied to the distal end of a limb. More particularly, when used on the arm, i.e. for the movement of shoulder and/or arm, the device is applied to the lower arm. The distal end of a limb is a lower arm in case the limb is an arm and a lower leg comprising the shin and the calf in case the limb is a leg. A proximal end of the limb is an upper arm in case the limb is an arm and an upper leg or thigh in case the limb is a leg. The brace supports the distal end of the limb.

The invention relates to a device, which facilitates the recovery and rehabilitation of one or more limbs and/or joints after injury, disease, surgical operations or other problems. In particular, the device can be used to impose a continuous passive motion, "CPM", to a limb and/or joint. CPM is defined as a continuous mechanical stimulation of the movement of a joint and/or limb, in consideration of a patients' tolerable motion. The term "passive" refers to the absence of active participation to the movement by the patient.

Continuous passive motion therapy has been found to have beneficial results in the rehabilitation of injured limbs. CPM improves the healing of tendons and ligaments, enhances the metabolism of a joint, improves resorption of effusions and may prevent and even overcome joint stiffness as well as secondary arthrosis, muscle atrophy and soft tissue contracture. CPM preferably provides a patient with anatomically correct motion that essentially duplicates the normal rhythm of the affected joint. Passive motion is also used for treatment of other bone and muscular disorders, such as arthritis and muscular dystrophy.

In the following description, the device according to the invention will be described with regard to its application for providing CPM to an injured shoulder and an arm connected thereto but the present invention is not limited thereto. A continuous mechanical stimulation of the movement of joints, in this case an elbow and shoulder joint in consideration of a patient's tolerable motion, is obtained. However, as it should be understood from the invention, the application of the device according to the invention is not limited thereto.

The device enables the embraced arm and shoulder, although immobilized, to perform a number of different kinds of automated passive arm movements. This device provides a particularly effective rehabilitation of shoulder and arm injuries. It shortens the rehabilitation time in general and shortens the hospital and the time of treatment, which is an important economic factor. The present invention provides a device which enables the shortening of the period of treatment of an injured shoulder, preventing joint stiffness and maintaining effective joint movement.

The device according to the invention fits against the lateral portion of the torso under the shoulder of a patient carrying the device and provides support for the upper arm and the lower arm or forearm. Importantly, the device enables the embraced arm and shoulder to undergo a maximal possibility of movements of arm and shoulder over a broad range of angles and planes. As will be understood, the angles and linear displacements of the arm and shoulder will depend on the ergonomic limitations of each patient individually.

Figure 1:
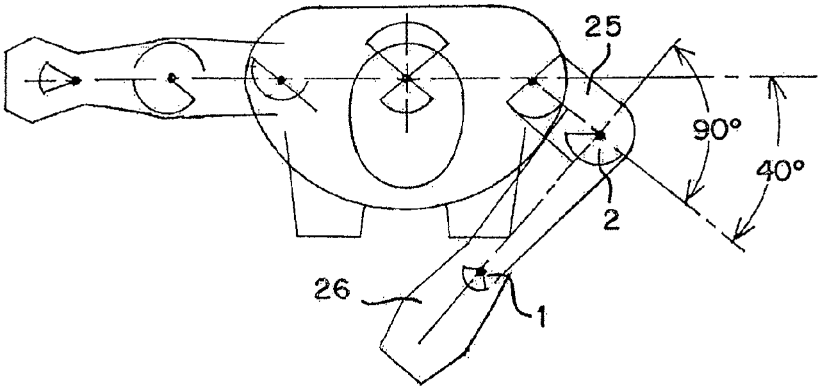
FIG. 1 represents an upper view of the basic geometry of the lower and upper arm on a human body. The two points of control of movement are located near the wrist and near the elbow.

A basic geometry for an upper arm (25) and a lower arm (26) is represented schematically in FIG. 1. As a starting point for the mechanical arm support system and the movement concept in general, the elbow position comprises an angle between the lower arm and the upper arm of 90° or less. The position of the lower arm is comprised within a horizontal plane, further referred to as the "neutral horizontal plane". The neutral position of the arm, viewed from above as represented in FIG. 1, may consist of a position of the upper arm of about 40° in relation to the shoulder line and a position of the elbow at an angle of about 90° in relation to the shoulder.

The device according to the invention enables different types of movement to be performed by the arm and shoulder. All movements can be converted to linear displacements. The motor mechanism of the invention meets this requirement, regardless of the ergonomic group. The underlying mechanism of the device allowing the passive motion movement is related to two "points of movement control". The "points of movement control", herein also referred to as the "points of control", are located on the lower arm section of the mechanical arm support and include a point of control of the wrist 1 and a point of control of the elbow 2. The exact location of the points of control is not critical and does not have to be exactly under the joint of the limb. Thus, the control point of the wrist (1) can be situated near the fingers, under the palm of the hand or closer to the point of control of the elbow. Hereinafter, these movement control points as described above will be referred to as 'point of control of the wrist' and 'point of control of the elbow'.

Figure 2:
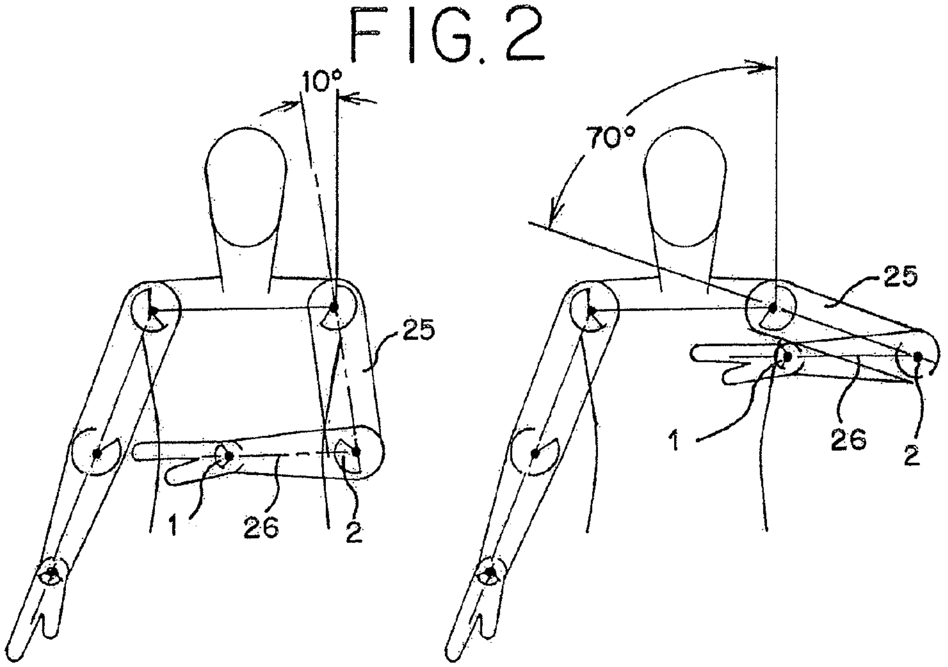
FIG. 2 represents a front view of two basic geometries of the lower and upper arm on a human body during adduction or abduction movement

The different movements of an arm contemplated in accordance with the present invention, can be described as follows:

A first type of movement includes abduction and adduction movement. "Abduction" and "adduction" refer to the movement of the arm away from and towards the median axis, or long axis, in the median plane of the body. The "median plane" of the body is defined by the front or back of the body in a straight position. "Abduction" is the movement away from the median axis, such as raising an arm laterally or sideways. "Adduction" is the opposite movement, i.e., movement towards the median axis of the body. Adduction and abduction are herein defined as the parallel movement of both points of control. According to the invention, adduction or abduction, i.e. glenohumeral movement, can be performed over an ample range of angles, i.e. between a small starting angle, amongst others determined by the thickness of the portable device and an end angle, determined by clinical relevance. This range technically can go up to at least 90°, but preferably is between a start angle of 10° and up to an end angle of 70°, which is, in most cases, the clinically relevant range. An example of the abduction or adduction movement is shown in FIG. 2, showing two positions of the arm during the abduction or adduction movement of a person's arm. In adduction and abduction movements, the lower arm (26) is moved towards or away from the body while the lower arm (26) stays in an essentially horizontal position, as both control points of the lower arm are subjected to a parallel movement.

A second type of movement includes the rotation of wrist (1) and elbow (2). During rotation of the wrist the point of control of the elbow is immobilised and the point of control of the wrist moves up and down versus the neutral horizontal plane. It is to be noted that this movement does not influence the wrist joint, and the wording "rotation of the wrist", refers to rotation of the lower arm (26) whereby the rotation is caused by movement of the control point positioned near or at the wrist (1). The wrist joint is not trained in this movement, as the hand and the lower arm are immobilised together on a lower arm support. During the rotation of the elbow, the point of control of the wrist is immobilised and the point of control of the elbow (2) moves up and down versus the neutral horizontal plane. The degrees of movement for the rotational movement are comprised between anatomically relevant angles, e.g. between about 30° up and about 30° down with relation to the neutral horizontal plane. The above mentioned angles are also determined by the specific anatomy and clinical circumstances of the user. The rotational movements are caused by a linear displacement of one of the control points by a suitable actuator or actuators, which will be in the range of 250 mm up to 300 mm. For instance, when the neutral position of the lower arm is set at horizontal (0°), the point of control of the wrist on the lower arm can move 30° up and 30° down in relation to the neutral horizontal plane, the elbow/shoulder axis acting as hinge.

A third type of movement includes a combined movement of both wrist and elbow by alternating movement of both points of control versus the neutral horizontal plane. The movement of the wrist and the movement of the elbow occur at the same time but in opposite directions. For this combined movement, the virtual rotation point is situated in the middle of the lower arm. The maximum deflection can vary between about 40° and about 60°, depending on the anatomy of the human body of the user and the clinical relevant motions in correspondence with the injury.

Figure 3:
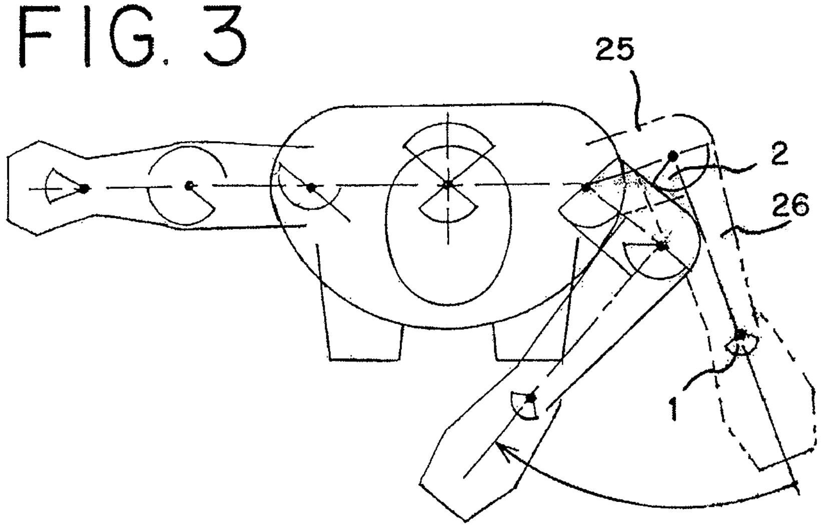
FIG. 3 represents an upper view of the basic geometry of the lower and upper arm on a human body during exo/endo rotation.

A fourth type of movement involves the movements of exo/endo rotation, i.e. the movement of antepulsion and retropulsion (see FIG. 3). The terms "external rotation" or "exo rotation" or "retropulsion" are used as synonyms herein and refer to rotation away from the median axis of the body. The terms "internal rotation" or "endo rotation" or "antepulsion" are used as synonyms herein and refer to rotation toward the median axis of the body. These movements take place in parallel with the neutral horizontal plane. In other words exo rotation and endo rotation refers to the rotary movement around the longitudinal axis of the bone in the proximal end of the limb, respectively away from or towards the centre of the body, thereby turning the proximal end of the limb respectively outward or inward. The endo/exo rotation movement will be induced by a linear displacement of up to 300 mm. An illustration of endo/exo rotation movement of an arm is given in FIG. 3. Two positions of the arm are shown during endo/exo rotation movement. The angle between the upper arm and the lower arm is locked mechanically during endo/exo rotation movement. If the upper arm and the lower arm are not mechanically locked, i.e. if the angle between the upper arm and the lower arm is allowed to vary, the same linear displacement of up to 300 mm can cause translational movement of the lower arm.

A patient can go through a series of such arm movements, which can be adjusted in terms of the type of movement, the alternation of the movements and their speed. Importantly, according to the device of the invention, the shoulder joint has no mechanical hinge or other kind of support. The type of movements a patient should undergo can be programmed, due to the use of a programmable motor mechanism. Unexpectedly, single as well as combined movements can be performed when using the device according to the invention. Although all the above-described movements include very different motions, such as translational as well as rotational movements, they can optionally all be performed using a device of the invention driven by a drive means such as a motor mechanism. Also, the degree of motion can be adjusted by the motor mechanism, e.g. by means of a control unit which may be set or adjusted to make the drive means perform a certain degree of motion. In addition, no extreme movements are imposed upon the patient. Such extreme movements may cause more harm than good. Importantly, as they are optionally motor-driven, all movements can be performed in a controlled way and the patient can stop the automatic movement at any time.

Figure 4:
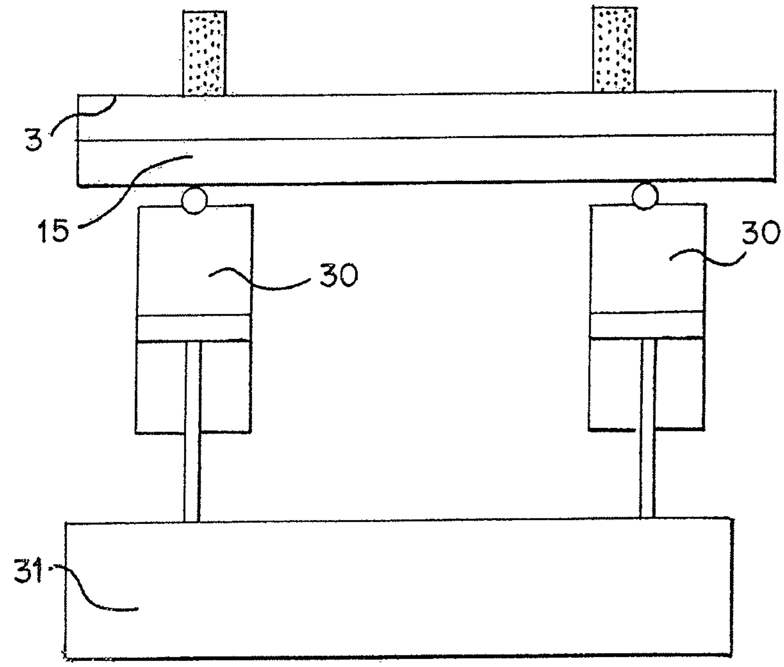
FIG. 4 represents a schematic view of some of the basic components of a portable device according to an embodiment of the present invention.
Figure 5:
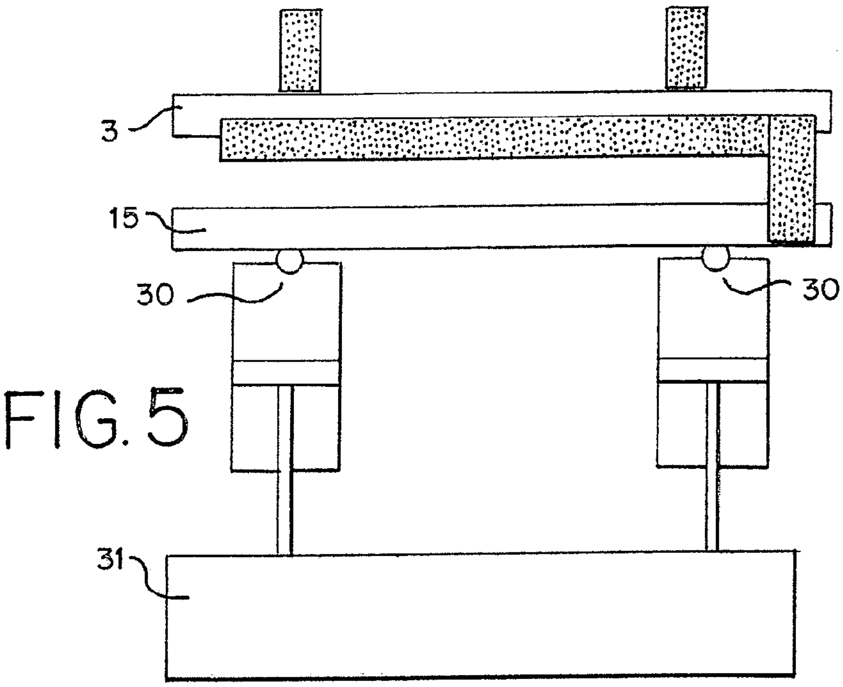
FIG. 5 represents a schematic view of some of the basic components of a portable device according to another embodiment of the present invention.

FIGS. 4 and 5 give a schematic representation of two embodiment of the present invention A device is shown having two actuators (30) at least one of which is connected to a drive means or motor unit ensuring the linear, also called vertical, extension of (at least one) actuator (30). The motor may be a part of a programmable motor (31). The actuators (30) are connected to a secondary sub-frame (15). This can be either connected directly to a primary sub-frame supporting the lower arm (3) as shown in FIG. 4, or, alternatively, can be connected to a primary sub-frame supporting the lower arm (3) by a mechanical interface (14), as shown in FIG. 5. The two connection points between the actuators (30) and the secondary sub-frame (15) represent the two points of control of the lower arm (26): the linear movements performed by the actuators (30) are also performed by the lower arm (26) which is immobilized on the support (3). Similarly, if the connection between the secondary sub-frame and the primary sub-frame supporting the lower arm is made by means of a mechanical interface (14), the movements of the point of control of the wrist (1) and the point of control of the elbow (2) are transferred from the secondary sub-frame to the support of the lower arm. The actuators (30) can each either be immobilized, leading to rotation of the lower arm (26) if the other actuator (30) is extended or its length is decreased, or they can be allowed to move in parallel with each other (30), leading to a horizontal movement of the secondary sub-frame (15).

According to a particular embodiment of the invention, the motor has two motor units, connected to and driving the movement of an actuator (30). For example, in this embodiment one motor unit ensures the movement of the point of control of the wrist and the other unit ensures the movement of the point of control of the elbow.

Each of the motor units ensures a vertical movement of the actuators (30), i.e. extension along the axis of the actuators (30), allowing several types of movements.

A parallel movement of the secondary sub-frame and consequently of the lower arm is performed when both actuators are evenly changed in length at the same time. This corresponds to the abduction and adduction movements of the arm. When only one of the actuators is moved, a rotational movement of the lower arm is obtained, corresponding with rotation of the wrist (1) or the elbow (2) as described above. In order to allow rotation of about 30° upwards and about 30° downwards from the neutral horizontal plane, the rest position of the lower arm (26) is preferably such that the length of the actuators 30 is somewhere in the middle of their fully extended length so that the length of the actuator can both be reduced, corresponding with a rotational movement downwards and extended corresponding with a rotational movement upwards. Alternatively, if considered clinically relevant, this rotational movement can also be performed in another way: when the rest position of the arm is set to the position corresponding with both actuators (30) being at minimal (or at maximal) length, rotation over approximately 60° can be performed by extending (or reducing the length of) one of the actuators (30). The third type of movement described above, which is a combined movement of wrist and elbow, is obtained when both actuators are used at the same time with their length being changed in opposite directions.

Alternatively, it can be envisaged within the context of the invention that only one of the actuators (30) is motor-driven. According to this embodiment, the abduction/adduction movements are ensured by allowing the non-motorized point of control to move in parallel with the motorized point of control. The rotational movements in such a device are ensured by fixing the non-motorized point of control at a certain point while the actuator of the motorized point of control moves upward and downward.

According to a further embodiment of the invention, the device comprises a first primary sub-frame for supporting the distal end of the limb and a secondary sub-frame and a third motor unit is provided in the mechanical interface (14), under the primary sub-frame. This third motor unit ensures the movement of the support of the lower arm in the direction of its longitudinal axis, as indicated by the arrow 17 in FIG. 9. This movement ensures the translational movement of the lower arm, which in combination with a rotational movement around the control point of the elbow allows exo/endo rotation.

The device of the invention can be secured to the limb, e.g. arm, by means of a brace (92). The brace (92) may comprise besides a lower arm support (3) for supporting the lower arm of a user, also an upper arm support (4) for supporting the upper arm of a user. The lower arm support is attached to the upper arm support (4) by a hinge (5).

Flexible positioning means can be used for positioning the brace (92) and the motor unit on the body of a person carrying the device in a stable position. For example, the positioning means (7) can be an inflatable housing of flexible material provided with a hip fastening means (22) (FIG. 6). The housing allows at least partial deformation when it is fastened on a body for providing a stable position. Due to its specific arrangement, the device has the advantage of not sliding from its optimum position to the back of the human body, a disadvantage that occurs in many of the known prior art systems.

FIGS. 6 and 7 give a more detailed illustration of a embodiment of the device according to the invention, hereafter illustrated for the use on an arm. The device according to the invention immobilises the upper arm (25) and the lower arm (26) by means of an adjustable mechanical support system, comprising a lower arm support (3) and upper arm support (4) each provided with a primary sub-frame and arm fasteners (10). Two simple structures made form a suitable material such as plastic support the upper and lower arm. A simple frame made form a suitable material such as metal, preferably aluminium, reinforced carbon fibre composite etc., supports the plastic support structures, i.e. the “primary sub-frames”. The angle between lower arm (26) and upper arm (25) is controlled by the mechanical hinge (5). This hinge is geometrically located under the patient’s elbow. The mechanical hinge can be adjusted, continuously, and locked mechanically. By providing the mechanical hinge point under the elbow, physical contact with the elbow is avoided and thus also injuries that might occur due to physical contact with the elbow are avoided. The lower arm support of the brace thus is provided with a first primary sub-frame (3) and two arm fasteners (10); and said upper arm support is provided with a second primary sub-frame (4) and an arm fastener (10). Hereinafter, with regard to mechanical movement of the device, when primary sub-frame is mentioned the primary sub-frame of the lower arm is intended.

In some cases, the arm fasteners (10) are equipped with fixing straps (12). These allow a better immobilization of the limb. According to a particular embodiment of the invention, the lower arm support is further provided with a hand support cushion (13), being provided at the end of said support. This hand support cushion (13) prevents stress-points on the patient’s arm tissue. The arm fasteners (10) and hand support cushion (13) provide support for the wrist and the hand. The patient’s hand will therefore not hang down, a process which may cause discomfort, injury, or loss of circulation.

In another preferred embodiment the portable device according to the invention comprises a device wherein the lower arm support (3) is adjustable in order to fit the length of the upper and the lower arm of a user. The target group for use of the device of the invention mainly consists of adult men and women of the 5% to 95% ergonomic groups. As a consequence it is preferable that the device of the invention is adjustable to every such patient. Several features of the device enable the independent adjustment and personalisation of the brace (92). For example, the arm members are fixed on the plastic support structures by means of simple straps (12). The plastic support structures can be adjusted in position to fit the upper and lower arm. The position of the hand support versus the lower arm support can be adjusted lengthwise. Consequently, the device is comfortable from a patient's point of view and is easy to apply. Additionally, the arm and shoulder brace is adjustable for a patient's length, body and anatomy and is adjustable with respect to speed and range of motion. All these features allow the device of the invention to be independently adjustable for use with either shoulder. Also, as mentioned above, the positioning means of the device consists of an inflatable housing of flexible material provided with a hip fastening means, e.g. a belt, said housing allowing at least partial deformation when fastened on a body for providing a stable position. Optionally, in another embodiment, the portable device according to the invention may further comprise belts provided with fasteners. The weight of the arm and the overall mechanical system of the device itself is supported by the positioning means, e.g. an inflatable air chamber (7). The inflatable air chamber (7) is kept in place with relation to the patient's body by means of a hip belt and optional belts with simple fasteners, e.g. Velcro. The fact that the positioning means consists of a flexible material involves several advantages. The positioning means is deformable under the weight of the brace and motor mechanism thereto connected. Also, it can easily adapt to the anatomy of a patient carrying the device. Furthermore, it can take in a comfortable position along the torso of a patient carrying the device.

According to a particular embodiment of the invention, the mechanism responsible for the movement of the points of control can comprise a secondary sub-frame (15), and two motor units. The "secondary sub-frame" (15) is defined as the frame that links the point of control of the wrist (1) and the point of control of the elbow (2). Different types of movements can be performed using this mechanism:

a) If the two control points are moved in parallel an adduction/abduction movement is performed.
b) If only one of the two control points is moved, there is rotation of the wrist only or rotation of the elbow only. For rotation of the wrist only, the control point at the elbow is immobilised and the control point at the wrist is moved. It is to be noted that this does not allow exercising of the wrist (1) joint, as the hand and the lower arm are immobilised together. This motion implies a rotation around the elbow (2). Rotation of the elbow (2) only is performed by immobilising the wrist (1) control point and moving the control point at the elbow (2).
c) If both wrist (1) and elbow (2) are moved at the same time but in opposite directions, this is called complex rotation movement of wrist (1) and elbow (2). The drive mechanism that enables the movement of the points of control is preferably located in the zone between the mechanical support of the arm, i.e. the primary sub-frames with plastic support structures, and the air chamber, as indicated on FIG. 6. In another embodiment, the secondary sub-frame linking both points of control has a mechanical transition (14) to a primary sub-frame. The connection between the secondary sub-frame and the primary sub-frame is provided by the mechanical interface (14), which is e.g. a hinge-like structure along the vertical axis, located at the patient's elbow. An illustration of an embodiment wherein the support of the lower arm is connected by a mechanical interface to a secondary sub-frame is provided in FIG. 7. The motor mechanism used in order to ensure abduction/adduction and rotational movements by the device of the current invention can be any type of mechanism that allows controllable movement of the two control points. This movement control can be performed by e.g. a set of inflatable air chambers, whereby two separate inflatable air chambers can allow movement of the two control points. In this case an air pump or compressor is necessary in combination with separate inflatable air chambers or with air pressure pistons. Alternatively, the controllable movement of the two control points can be performed by spindles, linear actuators or mechanical piston systems. Preferably this is performed using spindles driven by a motor unit being an electromotor allowing vertical movements of the actuators 30. Preferably two motor units are provided in the motor mechanism, whereby one motor unit or first unit is provided for the wrist point of movement control and the other unit or second unit is provided for elbow point of movement control. Both motor units induce movements in a vertical direction. This vertical direction is referred to the axial direction of the motor unit, as can be seen on FIG. 6 and FIG. 8, not to e.g. the median axis of the body. In a particular embodiment, the invention relates to a portable device, wherein the first and second motor unit consists of a triple spindle (90) with electromotor with worm wheel transfer (91), being provided in a housing, allowing the motor units to induce a vertical movement of the actuators (30). Parallel extension of the two motor units in this case allows performing adduction/abduction movement, while extension of only one motor unit or unequal or non-equivalent extension of the two motor units allows performing rotation movements. The strength of the motors used is adjusted so that they can deliver sufficient power to allow vertical movement of the extending actuators under the pressure of the limb resting on the motor units.

In another preferred embodiment, the motor mechanism of the invention is at least partially provided in a protecting structure, for instance a bellows structure. The protecting structure not only protects the drive mechanism but also provides protection for the brace user from being harmed by the mechanism. In the interests of safety, it is an advantage for the CPM device to be designed so that a minimum of the drive mechanism is exposed. If the operating parts of the device are concealed, and in the present invention even partially provided in the air chamber element, it reduces the risk of a patient's being pinched by a part of the machine, or foreign bodies such as bed clothes or personal clothing from getting caught in the mechanism. The bellows structure is preferably constructed from lightweight plastic. As it will be understood, the portion of the motor mechanism not provided in this protecting structure is provided within the positioning means.

In another embodiment, the portable device also comprises a safety device so that the motion is stopped, if a patient uses his muscles to counter the movement, e.g. if the movement causes severe pain. Countering of the movement leads to an increased torque on the motor. Sensing of an increased torque on the motor thus can be used to trigger this safety procedure.

As mentioned above, the device of the invention optionally can further comprise a mechanical interface, which causes the secondary sub-frame to interact with the primary sub-frame of the lower arm support. In a preferred embodiment, this mechanical interface is provided with a motor-driven sliding mechanism, said mechanism allowing the lower arm support to perform a sliding movement. If the mechanical lock of the hinge (5) between the upper arm and the lower arm is loosened, this allows translation of the lower arm, whereby the angle between the upper arm and the lower arm changes. In this way, motor driven translation of the lower arm is performed. Preferably, the mechanical interface 14 is a hinge-like structure, which is located at the patient's elbow between the primary and the secondary sub-frames.

The hinge-like structure optionally allows rotation of the primary sub-frame. Thus, it can be envisaged that the hinge allows the primary sub-frame to be fixed parallel to the secondary sub-frame (15), or rotated over a fixed angle with the elbow control point as rotation centre or set as a rotatable hinge.

With a fixed angle between the lower arm (26) and the upper arm (25), i.e. when the hinge (5) between the lower arm and upper arm is mechanically locked, the sliding movement of the arm induced by the motor-driven sliding mechanism induces rotation around the elbow control point leading to the exo/endo rotation movement of arm and shoulder. Thus, the motor-driven sliding mechanism combined with the rotatable hinge-like mechanical interface enables the exo/endo rotation movement of arm and shoulder.

The motor provided for the sliding mechanism can be any type of motor allowing sliding movement of the lower arm (26). The motor preferably is light and silent and is stoppable at any point. Preferably the motor is a triple spindle with electromotor.

A particular embodiment of the motor mechanism in accordance with the present invention is further illustrated on FIG. 8. The motor-driven sliding mechanism is located in a housing (14), and connected, via a secondary sub-frame (15), with the control point of elbow (2). A bellows structure (6) may be provided to protect the motor mechanism and to improve safety of the brace user. One motor unit, i.e., the first unit (8), is provided which controls the wrist movement (8) and another motor unit, i.e., the second unit (9) controls the elbow movement. In addition, a foam block (16) is optionally provided at the height of the hip. This block provides additional mechanical protection for a user of the device according to the invention and also provides protection for the air chamber unit of the device. The foam block avoids stress points on a user, which may be caused by contact of the user with the device according to the invention. The mechanical concept of the endo/exo rotation sliding mechanism is shown on FIG. 5, which gives a detailed view on the relation between the sliding movement of the lower arm (17) and the compensating rotation movement (18) during the exo/endo rotation. The sliding mechanism, i.e. conduction of the lower arm support (3) according to arrow 17, is combined with a rotation point near the height of the elbow point of movement control, according to arrow 18.

In a particular embodiment, the motor units for the control points near the wrist (1) and elbow (2) consist of a triple spindle (90) with electromotor, which are mounted in a plastic housing. The motor units have compact electromotors with worm wheel transfer (91). This concept enables controlled movements that are stoppable at any point. Furthermore spindles with electromotors have the advantage that they are quite silent, they are relatively cheap and the speed of the device is easily controllable. Therefore, the device of the invention allows movements of the limbs to be performed in a controllable and preferably in an automated way.

According to a further embodiment of the invention, a part of the drive mechanism is located in the space defining the envelope of the positioning means (7), e.g. an air chamber, as shown on FIG. 6. The result is a very compact device. Surprisingly, this arrangement does not hinder the functionality of the positioning means (7), i.e. a supporting and damping function of the air chamber. The linear movements of the points of control, in case of alternating movements, i.e. combined movements, results in a marked angle deviation (rotation) of the motor mechanism. This will be compensated by a flexible suspension of the motor mechanism in the air chamber, without compromising the function of the air chamber. In other words the angle deviation will at least be partly captured by the flexibility of the direction of the motor, as it is mounted floating in the flexible positioning means. More specifically, the motor is connected to the inflatable air chamber at the upper side of the inflatable air chamber, i.e. where the motor protrudes from the inflatable air chamber. As the motor is not connected to the bottom or sides of the inflatable air chamber and as the inflatable air chamber is a flexible means, this allows a degree of flexibility in the angle of the motor with respect to the vertical axis of the body. Furthermore, the connection of the vertical extending units of the motor to the frame connected to the lower arm preferably is performed using adjustable ball fittings with a limited degree of freedom.

In a preferred embodiment, the device according to the invention further comprises a remote control unit. This remote control unit (19) is compact, comprising control switches and a display screen, for example but not limited to an LCD screen, and can be plugged in by means of an electric cable. Preferably, medical personnel determine the maximum range of abduction/adduction or rotation within which the injured shoulder should be exercised. The limits of these movement degrees are inputted to a microprocessor of the remote control unit. The control unit is designed to operate in a manual or automatic mode selection of the operating mode being controlled by the patient via switches on the control unit. In an automatic mode used for continuous passive motion the control unit continuously operates the motor unit to perform the desired movements of arm and shoulder between the preset limits. Thus, in the automatic mode the shoulder can safely and continuously undergo programmed passive movements. Furthermore, the device according to the invention is provided with two compact connectors (20), (21), provided at the upper side of the positioning means (7), whereby one connector is connected to the remote control unit (19) and the other connector is connected to an electric transformer (28) or batteries (27). Optional batteries can be plugged into the air chamber's electrical interface. These batteries provide a minimum of autonomy in case power voltage is not available. In the other case, a compact transformer is used. As a consequence, the arm and shoulder brace of the invention is designed in such a way to allow sufficient autonomy of the device.

Apart from the adjustability to the patient's individual anatomy, another important feature comprises the fact that the device is built in such a way in order to be easily adapted for use with a right or a left limb, i.e. for example for use with the right shoulder as well as the left shoulder. The flexible immobilization of the left arm can be done in the same conditions and in symmetric way for the right arm. The following features enable this right and left arm use. The plastic supports supporting upper and lower arm and the underlying primary sub-frames have a symmetric design. Also, the elbow hinge point turns in such a way that the device is adjustable for the left as well as the right arm. Furthermore, all other interfaces are built symmetrically or enable easy adjustment for left or right use.

As mentioned above, the device is light and portable. This feature enables the device to be transported from room to room in order to enable different patients to share the CPM device. Also, it is of even further advantage that the device is designed to allow the patient to wear the device since the patient may be subjected to continuous treatment. The patient may thus remain mobile while being subjected to CPM treatment. This facilitates treatment, which may last for several hours or longer per session. Another feature is that the arm and shoulder brace is useable in every day circumstances and it can already be used immediately after an operation even before the user has regained consciousness. As it is important that the device is portable, both from the standpoint that it is possible that it must be carried from room to room in the hospital, and also that it is of an advantage to provide a device which allows a certain amount of mobility for the user, the device is designed to be as light as possible. Thus, where it is possible, the parts such as the lower and upper arm supports, the bellows structure concealing the drive mechanisms, are constructed of light weight material, preferably of a lightweight rigid plastic. In addition, also from an ergonomical point of view, the device of the invention has several innovative characteristics. Importantly, the device avoids the presence of any support, i.e. stress points, on or next to the injured shoulder. The arm and shoulder brace has support structures, which do not cause any “pressure points”. Amongst these structures are the hip, hand and arm supports, the hand cushion and the inflatable air chamber. Also, the hand support on the device is parallel with lower arm, which is important from ergonomic point of view, as it avoids an hanging off of the hand and injury of hand and wrist, which may result in a bad circulation and oedema. Furthermore, the device is provided with several belts, which are easy and unambiguous to use. Importantly, these belts do not cross the breasts, which may be sometimes painful. The specific characteristics of the device combined with the belts makes it possible to use the system without it sliding off to the back of the user, a well known problem for several prior art devices.

In another embodiment, the invention relates to the use of the portable device according to the invention for medical application. In particular, the invention relates to the use of the portable device according to the invention for orthopedic treatment of arm and shoulder injuries. Use of the device can be envisioned as follows. The device is adjusted to a particular user. The device is then activated for continuous motion of the user’s shoulder, causing both abduction and adduction and rotation. The proper periods of treatment are to be determined by the medical personnel. The machine may also be used while the user is asleep.

The many advantages and innovative characteristics of the arm and shoulder brace according to the invention render the device particularly suitable for use in paramedical and orthopedic applications.

While the invention has been shown and described with respect to a particular embodiment thereof, this is for the purpose of illustration rather than limitation, and other variations and modifications of the specific embodiment herein shown and described, all within the intended spirit and scope of the invention, will be apparent to those skilled in the art.

The invention claimed is:

1. A portable device for providing continuous passive motion, the portable device comprising a brace and a drive mechanism, wherein:

the portable device is adapted for providing continuous passive motion of a limb of a human or animal body having a torso, the limb comprising a distal end and a proximal end, the distal end being connected to the proximal end with a first joint, the proximal end being connected to the torso with a second joint, the brace is adapted for supporting the distal end of the limb;

the drive mechanism is adapted for providing a settable continuous passive motion of the first joint and/or the second joint of the limb, said drive mechanism being coupled to said brace and controlling movement of the distal end of the limb;

the drive mechanism being adapted for controlling said passive motion simultaneously in a first control point and a second control point adapted to be placed at different locations on the distal end of the limb; and said drive mechanism comprises a first unit for controlling a first actuator configured for linearly displacing said first control point; said drive mechanism further comprises a second unit for controlling a second actuator configured for linearly displacing said second control point; and said portable device furthermore comprises means for flexible positioning said brace and said drive mechanism on a body of a patient, said means provided with means for flexible positioning for fastening said brace and said drive mechanism to the body of the patient.

2. A portable device according to claim 1, furthermore comprising means for immobilizing said second control point adapted to be placed on the distal end of the limb.

3. A portable device according to claim 1, wherein said flexible positioning means comprises an inflatable housing of flexible material said housing allowing at least partial deformation when said brace and said drive mechanism are the body for providing a stable position.

4. A portable device according to claim 1, wherein said brace comprises a first support adapted for the distal end of the limb, the first support being provided with a limb fastener; and a second support adapted for the proximal end of the limb, the second support being provided with a limb fastener.

5. A portable device according to claim 4, wherein said limb fasteners adapted for the distal end and the proximal end of the limb comprise fixing straps.

* * * * *